United States Patent [19]

Duthie, Jr.

[11] Patent Number: 4,976,739
[45] Date of Patent: Dec. 11, 1990

[54] IMPLANT SYSTEM

[76] Inventor: Robert E. Duthie, Jr., 9321 Warner Gulf Rd., Holland, N.Y. 14080

[21] Appl. No.: 338,543

[22] Filed: Apr. 14, 1989

Related U.S. Application Data

[63] Continuation of Ser. No. 863,371, May 15, 1986, abandoned.

[51] Int. Cl.$^5$ .......................... A61F 2/28; A61C 3/263
[52] U.S. Cl. ........................................ 623/16; 433/174
[58] Field of Search ........................ 411/411, 413, 416; 128/92 N; 623/16, 18, 19, 20, 21, 22, 23; 433/171, 172, 173, 174, 175, 176

[56] References Cited

U.S. PATENT DOCUMENTS

| | | | |
|---|---|---|---|
| 212,007 | 3/1938 | Adams | 32/10 |
| 581,335 | 4/1897 | Carr | 32/10 |
| 744,292 | 11/1903 | Carr | 32/10 |
| 1,060,568 | 4/1913 | Hurd | 32/10 |
| 1,089,201 | 3/1914 | Follows | 32/10 |
| 2,112,007 | 3/1938 | Adams | 32/2 |
| 2,793,884 | 5/1957 | Jungblut | 411/411 |
| 2,857,670 | 10/1958 | Kiernan, Jr. | 32/10 |
| 3,497,953 | 3/1970 | Weissman | 32/10 |
| 3,568,230 | 3/1971 | Rosan, Sr. | 10/86 |
| 3,589,011 | 6/1971 | Sneer | 32/10 |
| 3,590,485 | 6/1971 | Chercheve et al. | 32/10 |
| 3,987,499 | 10/1976 | Scharbach et al. | 623/18 |
| 4,051,559 | 10/1977 | Pifferi | 3/1.912 |
| 4,081,908 | 4/1978 | Sneer | 32/10 |
| 4,177,524 | 12/1979 | Grell et al. | 623/18 |
| 4,177,562 | 12/1979 | Miller et al. | 433/174 |
| 4,187,559 | 2/1980 | Grell et al. | 623/18 |
| 4,253,833 | 3/1981 | Edelman | 433/173 |
| 4,272,855 | 6/1981 | Frey | 623/18 |
| 4,324,550 | 4/1982 | Reuther et al. | 433/174 |
| 4,334,865 | 6/1982 | Borle | 433/174 |
| 4,416,629 | 11/1983 | Mozsary et al. | 433/174 |
| 4,431,416 | 2/1984 | Niznick | 433/174 |
| 4,531,915 | 7/1985 | Tatum, Jr. | 433/173 |

FOREIGN PATENT DOCUMENTS

| | | |
|---|---|---|
| 2615116 | 10/1976 | Fed. Rep. of Germany . |
| 1301471 | 12/1972 | United Kingdom ................ 411/411 |

OTHER PUBLICATIONS

Bofors Nobelpharma Brochure (date unknown).
Copyrighted, unpublished work of Applicant entitled TI-MAX-IUM Cranial Implant System with accompanying Copyright Registration Certificate No. TXU 192-718 (effective date of registration–Apr. 5, 1985).

*Primary Examiner*—David J. Isabella
*Attorney, Agent, or Firm*—Hodgson, Russ, Andrews, Woods & Goodyear

[57] ABSTRACT

An implant adapted for use in attaching a prosthesis to a bone features a screw threaded section characterized in that the thread roots and crests are of curvilinear section, wherein the roots have a radius of curvature essentially equal to twice the radius of curvature of the crests; a thread block section connected to the threaded section; a transversely enlarged flange section connected to the thread block section and formed with drive/lock recesses for facilitating threading of the anchor; a guide section extending from the flange section in a direction away from the threaded section; and a mounting opening extending through the guide, flange and thread block sections and into the threaded section for mounting a prosthesis attachment.

11 Claims, 3 Drawing Sheets

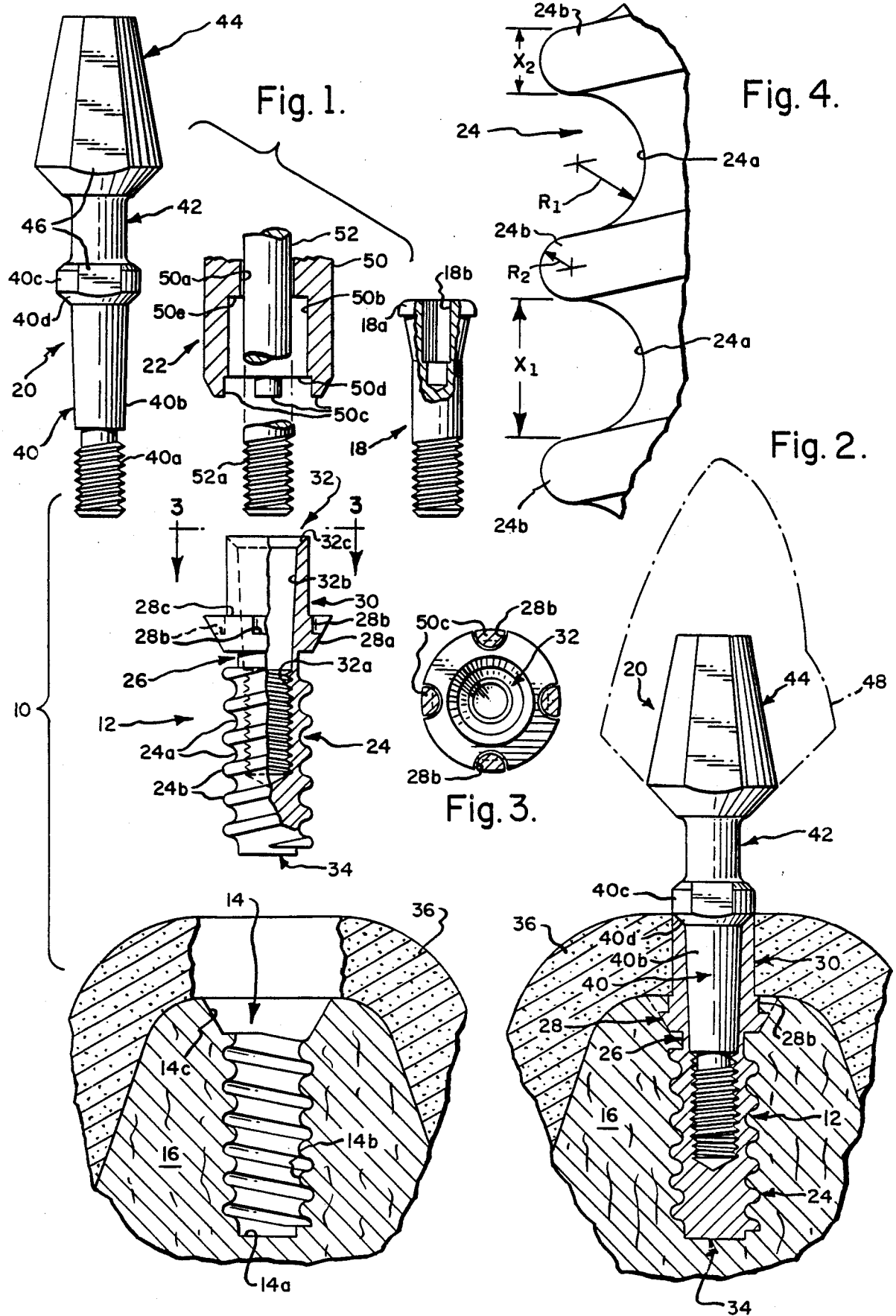

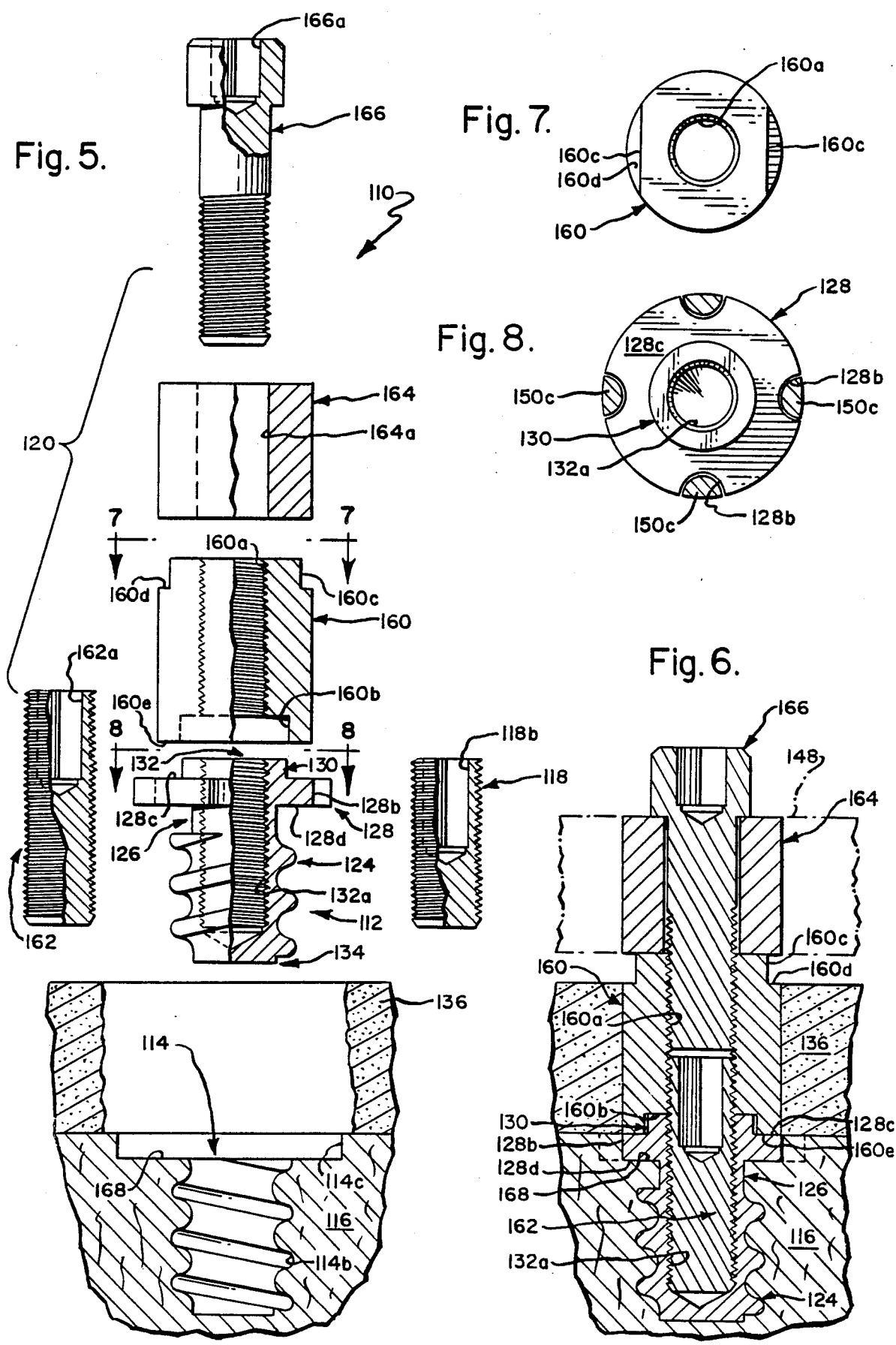

IMPLANT SYSTEM

This application is a continuation of U.S. patent application Ser. No. 863,371, filed May 15, 1986, now abandoned.

BACKGROUND OF THE INVENTION

The present invention generally relates to implants adapted for use in attaching a prosthesis to a bone.

It is well known to provide implants with screw threaded sections intended to retain an implant within a preformed hole provided in a bone; and to form such implants from a bio-compatible material intended to provide for healing osseointegration subsequent to implantation. Titanium is a particularly desirable implant material in that titanium oxide is capable of providing for an intimate bond or joint with bone matter incident to healing of the bone following implantation. It is desirable to pretreat the implant with a view towards increasing the rate of oxide formation, which otherwise occurs naturally to titanium in the presence of organic materials.

Heretofore, it has been common practice to provide implants with self-tapping screw threads with a view towards supplementing the holding power of the implant otherwise obtained from the growth of bone into cutting/locking recesses extending lengthwise of the threaded section of the implant, such as is disclosed for instance in U.S. Pat. No. 4,324,550.

Implants employing conventional screw threads often must be replaced, due to the shear failure of portions of bone engaged by the implant and/or due to failure of the bone to grow into uniform intimate contact with the implant adjacent areas where surface discontinuities are present in the preformed hole formed in the bone and/or the implant.

SUMMARY OF THE INVENTION

The present invention is directed towards an improved prosthesis attachment system having a reduced implant failure rate, as compared to prior implants of which I am aware.

More specifically, the present invention contemplates the utilization of a novel screw thread design for a bone implant, whereby uniform healing osseointegration is promoted throughout the extent of the threaded section of the implant. The present thread design is characterized in that the thread roots and crests are of curvilinear section, wherein the axial widths of the roots lie within the range of 1.5 to 2.5 the axial widths of crests. Preferably, the roots and crests are of essentially circular section, wherein the radius of curvature of the roots is essentially equal to twice the radius of curvature of the crests.

The threads of the implant are not capable of being self-tapping, and thus it is necessary to form an implant receiving hole in a bone, which has a diameter corresponding to at least the maximum diameter of the threaded section of the implant. It is preferred that the portion of the hole intended to receive the screw threads be provided with a size and shape, which is exactly complementary to that of such screw threads, so as to create a friction fit therebetween when the implant is threaded into inserted position. This provides for uniform and intimate initial metal to bone contact for purposes of promoting healing osseointegration throughout the extent of the threaded section of the implant without occasion for the forming of structurally weak fibrous capsules adjacent the implant. The smoothly contoured and mating threads of the implant and bone provide no surface discontinuity or localized compressive forces acting on the bone, which might otherwise retard or prevent desired bone growth.

The present implant possesses additional desirable features including the provision of a flange section and a thread block section serving to connect the flange section to the threaded section. The thread block section serves to provide a recess into which bone may grow for purposes of blocking unseating rotations of the implant threads and the flange section cooperates with the bone to prevent growth of skin into such recess, which might otherwise interfere with desired bone growth therewithin. The flange section also serves to provide a convenient drive connection for effecting driven insertion of the implant, wherein such connection defines additional recesses into which bone may grow for purposes of constraining implant rotation, and serves to supplement the holding power of the threaded section to prevent the implant from being "punched through" relatively thin bone structure, such as is present in the cranium.

The present implant also preferably includes a guide section projecting from the flange section and a mounting opening extending axially through the guide, flange and thread block sections and part way into the threaded section for receipt of a prosthesis mounting attachment.

In one form of the invention, the guide section projects from the flange section through a distance corresponding essentially to the thickness of skin covering the bone in the area in which the implant is to be inserted and the mounting attachment has one end shaped for receipt within the mounting opening, an opposite or head end for mounting a prosthesis and an intermediate or connecting portion, which is deformable for purposes of adjustably changing the orientation or placement of the head end relative to the axis of the implant, so as to allow for desired positioning of the prosthesis.

BRIEF DESCRIPTION OF THE DRAWINGS

The nature and mode of operation of the present invention will now be more fully described in the following detailed description taken with the accompanying drawings wherein:

FIG. 1 is an exploded view illustrating primary elements of an implant system according to the present invention;

FIG. 2 is an elevational view of an implant inserted within a jaw bone and with a prosthesis connected to the implant;

FIG. 3 is a view taken generally along the line 3—3 in FIG. 1;

FIG. 4 is an enlarged fragmentary view of the threaded section of the implant;

FIG. 5 is a view similar to FIG. 1, but showing an alternative embodiment of the implant system;

FIG. 6 is an elevational view similar to FIG. 2, but showing the alternative embodiment;

FIG. 7 is a view taken generally along the line 7—7 in FIG. 5;

FIG. 8 is a view taken generally along the line 8—8 in FIG. 5;

DETAILED DESCRIPTION OF THE INVENTION

Figure 9:
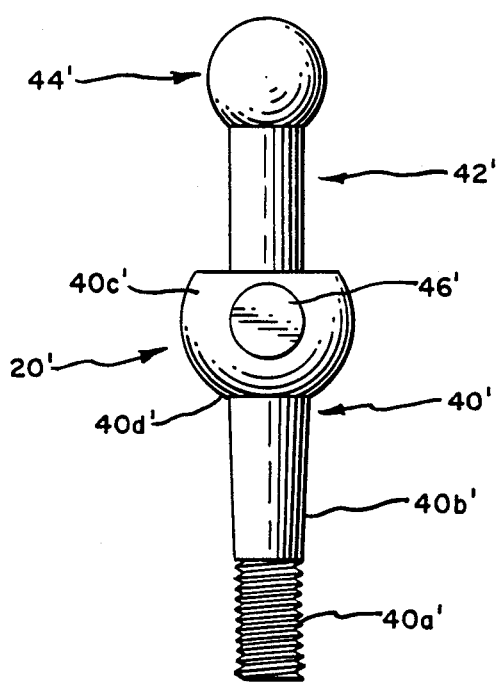
FIG. 9 is an elevational view showing an alternative embodiment of the prosthesis mounting post shown in FIGS. 1 and 2.

Reference is first made to FIG. 1, wherein elements of an intraoral implant system formed in accordance with the present invention are designated as 10. System 10 includes an implant or anchor member 12, which is intended to be placed within a preformed receiving hole or cavity 14 provided in jaw bone 16; a plug or closure 18; a permucosal attachment or prosthesis mounting post 20; and an implant inserting tool 22. Not shown are taps employed in the forming of hole 14.

Implant 12 is machined from a bio-compatible material capable of providing for maximum osseointegration subsequent to implantation. Commercially pure titanium is preferably employed to form implant 12, as well as other components of the system to be connected thereto, and the implant may be treated before implantation with a view towards increasing the speed of oxide formation thereon, which naturally occurs in the presence of organic matter.

Implant 12 is shown in FIGS. 1 and 2 as generally including a screw threaded section 24; a thread block section 26 joined to a relatively outer end of the threaded section; a flange section 28 joined to the thread block section; and a guide section 30 joined to the flange section. A mounting opening 32 extends part way axially through implant 12 and is defined by an inner threaded portion 32a, a conically shaped intermediate portion 32b and an outer conically shaped seal portion 32c. Preferably, a lead section 34 is joined to relatively inner end of threaded section 24.

Threaded section 24 is shown in FIGS. 1, 2 and 4 as having thread roots 24a and crests 24b, which are of curvilinear section, and which are joined by opposing parallel flanks as shown in FIG. 4, wherein the width of the roots $X_1$ lies within the range of about 1.5 to 2.5 the width of the crests $X_2$. Preferably, roots 24a and crests 24b are both of essentially circular section, wherein the radius of curvature $R_1$ or width $X_1$ of the roots is essentially equal to twice the radius of curvature $R_2$ or width $X_2$ of the crests with a view towards minimizing the volume of the implant in order to minimize the amount of bone required to be removed in forming hole 14. Below about $R_1 = 1.5R_2$, there would be insufficient thickness of bone between threads to resist shear failure of the bone, and above $R_1 = 2.5R_2$, there would be an insufficient number of screw threads to maintain the implant in seated position under load and/or the threads would be reduced to a thickness incapable of resisting expected shear loads imposed thereon during use of the implant. It is also anticipated that roots 24a may be of elliptical section, such that the roots may be slightly deeper or more shallow than that shown. However, deeper roots are not preferred in that the threads of implant 12 would have a greater tendency to fail, there would be insufficient structural wall thickness between the roots and mounting opening 32 and/or bone might not grow sufficiently into the root and a fibrous capsule might form. On the other hand, more shallow roots are not desirable, since there will be less surface area between bone and implant threads available to resist unscrewing of the implant. The maximum axial length of threaded section 24 is limited by the thickness of bone to be penetrated, whereas its minimum length is limited by the requirement that a sufficient number of threads be available for implant retention/anchoring purposes. As previously indicated, the threads of implant 12 are not capable of being self-tapping, and therefore the opposing parallel flanks provide power transmission in opposite directions.

Thread block section 26 and lead section 34, which are arranged adjacent the relatively outer and inner ends of threaded section 24, respectively, preferably have a diameter corresponding essentially to the minimum diameter of threaded section 24, as measured across roots 24a. The axial length of thread block section 26 would typically be essentially equal to or slightly less than about twice the root radius $R_1$, but in any event sufficient to permit bone to grow between thread section 24 and flange section 28, which is of sufficient thickness to effectively resist unthreading rotations of implant 12 after the healing of a patient is complete. The axial length of lead section 34 is chosen such that it will fill the void 14a formed adjacent the inner end of opening 14, as an incident to the opening forming operation to be described.

Flange section 28 is shown as having an overall diameter exceeding the maximum diameter of threaded section 24 and as being formed with a conically shaped seal surface 28a, whose minimum diameter corresponds essentially to the maximum diameter of the threaded section. The thickness or axial dimension of flange section 28 is chosen such that it corresponds essentially to the thickness of the cortical plate of jaw bone 16. Flange section 28 is also formed with a plurality of axially outwardly and radially outwardly opening drive/lock recesses 28b, whose purpose will hereinafter be discussed.

Guide section 30 has a cylindrically shaped outer surface whose diameter is slightly less than the maximum diameter of threaded section 24 and whose axial length corresponds essentially to the thickness of the gum 36 of a patient.

Plug 18 is sized to be removably threadably seated within mounting opening 32 for purposes of temporarily arranging its enlarged head end 18a in sealing engagement with the axial outer end surface of guide section 30 adjacent seal portion 32c of the mounting opening. Manipulation of plug 18 for purposes of threading same into and out of mounting opening 32 is facilitated by forming the plug with a non-round, e.g. square cross sectioned, drive recess 18b for receiving a like shaped drive tool, not shown.

Attachment 20 is shaped to define a mounting end portion 40, a cylindrical connecting portion 42 and a mounting head 44. Mounting end portion 40 is shaped and sized for receipt within mounting opening 32 and in this connection includes a threaded portion 40a adapted to be threadably coupled with inner threaded portion 32a, a conically shaped intermediate portion 40b adapted to be arranged in surface to surface engagement with intermediate portion 32b, and an enlarged seal portion 40c, which defines a downwardly convergent conically shaped seal surface 40d adapted to seal against seal portion 32c. The enlarged seal portion 40c and mounting head 44 are provided with "flats" 46 to facilitate gripping of attachment 20 by a suitable attachment drive or manipulating tool(s), not shown. The size and shape of mounting head 44 may be varied as desired to facilitate incorporation thereof within a desired prosthesis, such as a denture or single tooth 48 shown only in FIG. 2. The size of connecting portion 42 is chosen so as to allow bending thereof in order to vary the orientation of mounting head 44 and tooth 48 mounted thereon relative to the axis of implant 12 after the latter is permanently seated within hole 14, as required to insure proper positioning of tooth 48.

Implant inserting tool 22 is intended to be employed to pick up and then insert implant 12 within hole 14. The principal elements of tool 22 are shown in FIG. 1, as including a tool housing 50 and a rod 52, which is mounted for both rotary and reciprocating movement within bore opening 50a extending lengthwise of housing 50. Housing 50 is also provided with an end opening recess 50b, which is disposed concentrically of bore opening 50a and sized to sidably receive guide section 30 of implant 12; and a plurality of drive projections 50c, which are shaped and sized to be removably slidably received within drive/lock recesses 28b, when the lower end surface 50d of housing 50 bottoms out against the upper surface 28c of flange section 28 and/or when the closed end surface 50e of recess 50b bottoms out against the free upper end of guide section 30. The lower or free end 52a of rod 52 is threaded for receipt within threaded portion 32a of mounting opening 32.

To facilitate understanding of the invention, it is noted that implant 12 is drawn to scale in FIG. 1, but is substantially magnified in size. The illustrated implant is representative of several models of intraoral implants, which vary one from another primarily in the length of thread section 24. As by way of example, the implant depicted in FIG. 1 is a first or relatively short implant having an overall length of 0.370 inch, wherein the axial length of lead section 34, thread section 24, thread block section 26, flange section 28 and guide section 30 correspond to 0.010, 0.205, 0.020, 0.040 and 0.095 inch, respectively. Thread section 24 has twenty-eight threads per inch, a maximum diameter of 0.108 inch and values of $R_1$ and $R_2$ of about 0.0119 and 0.006, respectively. Seal surface 32c of flange section 28 forms an angle of thirty degrees with the axis of implant 12 and the surfaces of conically shaped portions 32b and 32c form angles of about one and a half and forty-five degrees with such axis. The maximum diameter of mounting opening portion 32b is 0.078 inch and the maximum diameter of threaded portion 32a is 0.058 inch.

In operation, hole 14 is formed in bone 16 by first preforming a drilling operation to create a stepped opening including a cylindrical inner part, not shown, which extends essentially axially co-extensive with the threaded portion 14b of hole 14 to be formed, and a conically shaped outer part 14c, which essentially corresponds in shape and size to implant flange section 28. Thereafter, the cylindrical inner part is progressively increased in size and shaped by use of a series of taps, not shown, until hole 14 assumes its final shape shown in FIG. 1. It is intended that threaded portion 14b essentially correspond in size and configuration with threaded section 24, so as to provide for close fitting or friction fit surface engagement therebetween, wherein bone 16 is not compressed by insertion of implant 12, and that outer part 14c provide for a close fitting surface to surface engagement with seal surface 28a.

After forming of hole 14, implant 12 is threadably inserted into the hole by use of tool 22. In this connection, threaded end 52a of rod 52 is first threaded into threaded portion 32a of mounting opening 32 for purposes of releasably attaching the implant to the tool and rod 52 thereafter slides within bore opening 50a until guide section 30 is arranged within recess 50b and drive projections 50c are arranged within drive/lock recesses 28b. Thereafter, tool housing 50 is manually rotated for purposes of threading implant 12 into hole 14. The threaded section 24 of implant 12 has a lead so that when threaded section 24 is rotated one revolution it moves into the site a distance equal to the screw pitch of threaded section 24. After insertion of implant 12, plug 18 is threaded into mounting opening 32 for purposes of sealing same and gum 36 is sutured to enclose the implant and plug. After a healing period of from about three to six weeks, the gum is incised to expose plug 18 and the plug removed and discarded. Plug 18 is then replaced by attachment 20, which again serves to seal off mounting opening 32, and connecting portion 42 deformed as required to properly position mounting head 44. A desired denture or tooth is then attached to mounting head 44 and gum 36 allowed to heal to complete the operation.

It is important to note that by providing threaded section 24 of implant 12 with smoothly curved or rounded surfaces and by forming threaded portion 14b of hole 14 in the manner described, intimate initial contact between metal and bone is achieved throughout the extent of the threaded section, so as to promote healing osseointegration or growth of the bone into an oxide layer formed on the surface of the implant in order to lock the implant in position. Thus, there is an absence of any surface discontinuity or stress area in the bone adjacent the threaded section or any void existing between metal and bone, which would inhibit bone growth and result in the creation of fibrous capsules serving to weaken the joint or bond between implant and bone. In like manner, intimate metal to bone contact is provided between outer part 14c and essentially the whole of seal surface 28a, except in the area of recesses 28b, for purposes of promoting healing osseointegration and to block the growth of gum 36 into mounting opening 32, such as would otherwise interfere with growth of bone into contact with the implant. Even though recesses 28b create surface discontinuities, the minimum radial depth of each recess, which would typically be about 0.020 inch, is such as to insure that bone will eventually grow sufficiently so as to substantially fill same, as depicted in FIG. 2, and create a lock tending to constrain rotation of implant 12. It will also be noted that by preventing growth of the gum into hole 14 past flange section 28, bone is allowed to grow into and substantially fill the shallow recess surrounding thread block section 26, whereafter such bone blocks unthreading of the implant.

A second embodiment of the present invention, which is shown in FIGS. 5–8, is directed to an extraoral or cranial implant system. In that this system is quite similar to above described system 10, the system shown in FIGS. 5–8 is designated 110 and like parts thereof, as well as corresponding portions of a patient, are designated by like numerals having the prefix "100". Thus, system 110 includes an implant or anchor member 112, which is intended to be placed within a preformed receiving hole or cavity 114 formed in the cranium 116; a plug or closure 118 having a non-round drive recess 118b; a percutanious attachment 120; and an implant inserting tool, not shown, which corresponds in overall structure to previously described tool 22, while being modified to interfit with the shape of cranial implant 112.

Implant 112 includes a screw threaded section 124; a thread block section 126; a flange section 128; a guide section 130; and preferably a lead section 134. A mounting opening 132 extends part way axially through the implant and is comprised wholly of a threaded portion 132a.

Threaded section 124 may be identical to threaded section 24 in all respects, except for its length, which is substantially limited by the relatively thin nature of cranium 116, as compared to jaw bone 16. In like manner, thread block section 126 and lead section 134 may be identical to thread block section 26 and lead section 34, except that the thread block section 126 may be of shorter axial length than thread block section 26 in order to maximize the length of threaded section 124 available for retention purposes.

Flange section 128 has an axial dimension less than that of flange section 28 in that it corresponds in thickness to the relatively thin cortical plate of the cranium. As such, it is not practical to taper its outer annular surface 128a to provide a seal surface, and thus the radial dimension of the flange section is substantially enlarged relative to that of flange section 128 in order to provide an annular or ring-like seal surface 128d facing axially towards threaded section 124. The relatively expansive nature of seal surface 128d, which extends radially outwardly of threaded section 124, additionally serves as a safety device for distributing external loads applied to implant 112 in order to supplement the holding power of relatively short threaded section 124.

Attachment 120 is shown in FIG. 5 as being of multi-part construction including a generally cylindrical spacer 160; a spacer connecting screw 162 having a non-round drive recess 162a; a cylindrical bushing 164 having an axially extending bore opening 164a and adapted for attachment to a desired prosthesis 148; and a bushing attachment screw 166 having a non-round drive recess 166a. Spacer 160 has an axially threaded opening 160a, an end opening recess 160b disposed concentrically of threaded opening 160a and sized to slidably receive guide section 130 and flats 160c for facilitating gripping/manipulation of the spacer.

In operation of the system shown in FIGS. 5-8, cranium 116 is drilled to create a stepped opening including a cylindrical inner part, not shown, which extends essentially co-extensive with the threaded portion 114b to be formed, and a cylindrically shaped outer part 114c, which has a diameter exceeding the diameter of flange section 128 and defines an axially facing seal surface 168. Thereafter, the cylindrical inner part is progressively increased in size and shaped by use of a series of taps, not shown, until hole 114 assumes its final shape shown in FIG. 5. As previously described with reference to implant 12, it is intended that threaded portion 114b essentially correspond in size and configuration with threaded section 124, so as to provide for a close fitting or friction fit therebetween.

After forming of hole 114, implant 112 is threadably inserted thereinto by use of a tool having drive projections 150c arranged for receipt within drive/lock recesses 128b, until the lower surface 128d of the flange section is seated in sealing engagement with seal surfaces 168. After insertion of implant 112, plug 118 is threaded into mounting opening 132 for purposes of sealing same and skin 136 sutured to enclose the implant and plug. After a healing period of from about three to six weeks, the skin is incised to expose plug 118 and the outer end of implant 112, whereafter the plug is removed and discarded. Plug 118 is then replaced by attachment 120, by the steps of threading screw 162 into mounting opening 132, threading spacer 160 onto screw 162 until the spacer engages and seals against the outer surface 128c of flange section 128, and finally employing screw 166 to clamp bushing 164 against the outer end of spacer 160, as shown in FIG. 6. Screw 166 may thereafter be removed whenever it is desired to remove prosthesis 148, such as for cleaning purposes. Screw 166 and bushing 164 may be replaced by other suitable attachment devices permitting ready removal of a prosthesis, such as may be defined by known snap-fit or magnetic devices, not shown.

It will be understood that spacer 160 may be provided in a series of standard lengths, as required to match the embedded length of the spacer, as measured between the bottom surface 160d of flats 160c and its lower end surface 160e, to the thickness of skin 136 present at any given point on cranium 116, as shown in FIG. 6.

As with the case of implant 12, the configuration of threaded section 124 of implant 112 and threaded portion 114b of hole 114, provides for initial surface contact between metal and bone, so as to promote healing osseointegration and retards the formation of fibrous capsules. In like manner, intimate metal to bone contact provided between surfaces 128d and 168 serves to both promote healing osseointegration at this point and to block the growth of skin 136 towards threaded portion 114b, where it would otherwise interfere with the growth of bone into the shallow recess surrounding thread block section 126. Further, as with the case of implant 12, the growth of bone into the recess surrounding the thread block portion 126 and into recesses 128b serves to provide positive locks resisting unthreading of implant 112 after healing of bone 116 is complete.

Figure 10:
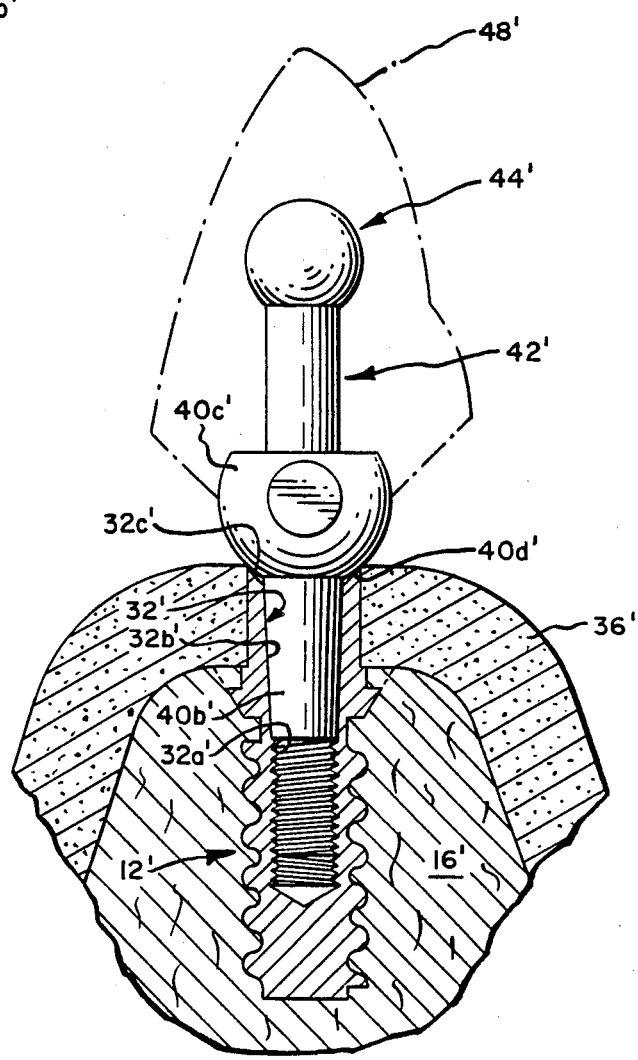
FIG. 10 is a view similar to FIG. 2, but showing the prosthesis mounting post of FIG. 9.

An alternative embodiment of a prosthesis mounting post is shown in FIGS. 9 and 10. In that this alternative mounting post is quite similar in construction to mounting post 20 depicted in FIGS. 1 and 2, and is adapted to be attached to the same implant, like primed numerals are employed in FIGS. 9 and 10. Thus, alternative mounting post 20' is shaped to define a mounting end portion 40', a deformable connecting portion 42' and a mounting head 44'. Mounting end portion 40' is defined by a threaded portion 40d adapted to be threadably coupled with inner threaded portion 32a' of mounting opening 32' of implant 12'; a conically shaped intermediate portion 40b' adapted to be arranged in surface to surface sealing engagement with intermediate portion 32b'; and an enlarged seal portion 40c', which has a generally spherical seal surface 40d' adapted to form a line contact seal against seal portion 32c'. Enlarged seal portion 40c' is provided with one or more "flats" 46' to facilitate gripping of post 20'. Post 20' principally differs from post 20 in that intermediate portion 42' is intended to be deformed, as required to vary the position of mounting head 44' relative to the axis of implant 12', prior to the application of tooth 48' to the post and in that the base of the tooth is intended to seal against seal surface 40d' in order to permit the tooth to be arranged close to gum 36' in the manner shown in FIG. 10.

While the invention has been described with particular reference to intraoral and cranial type extraoral implants, it is anticipated that the enlarged versions of such implants may be employed in connection with total prosthesis, such as a hip prosthesis.

I claim:

1. An implant for insertion within a complementarily shaped hole formed in a bone, said implant including:
a screw threaded section sized and shaped for receipt within said hole in uniform and intimate initial implant to bone contact for promoting healing osseointegration throughout the extent of said thread section without occasion for the forming of structurally weak fibrous capsules adjacent said implant, and characterized in the said screw threaded section has a smoothly contoured screw thread extending continuously throughout the length thereof, in that said threaded section has a lead so that when said threaded section is rotated one revolution it moves into a site a distance equal to the screw pitch of said threaded section, in that the thread roots and crests thereof are of curvilinear cross section, in that said thread roots and crests are joined by opposing parallel thread flanks which provide power transmission in opposite direction, and in that the width of said thread roots is greater than the width of said thread crests to promote healing and to provide force transfer without shear.

2. An implant according to claim 1, wherein the width of said thread roots lies in the range of about 1.5 to 2.5 the width of said thread crests.

3. An implant according to claim 1 wherein said thread roots and said thread crests are of essentially circular cross-section and the radius of curvature of said thread roots is essentially equal to twice the radius of curvature of said thread crests.

4. An integrally formed implant for insertion within a hole formed in a bone having a cortical plate and a skin covering of given thicknesses, said implant including:
a screw threaded section adapted to receipt within said hole and characterized in that the thread roots and crests thereof are of essentially circular cross section, wherein the radius of curvature of said thread roots is essentially equal to twice the radius of curvature of said thread crests;
a flange section;
a thread block section joining said threaded section and said flange section, said flange section having a transverse dimension exceeding the maximum transverse dimension of said threaded section, as measured across said thread crests, and said thread block section having a transverse dimension corresponding essentially to the minimum transverse dimension of said threaded section, as measured across said thread roots; and
a guide section joined to said flange section and extending axially away from said threaded section, said guide section has a transverse dimension less than said flange section, said flange section is formed with a plurality of drive member receiving recesses arranged transversely outwardly of said guide section, and said receiving recesses open axially and radially outwardly of said implant.

5. An implant according to claim 4, wherein said guide section has an axial length corresponding essentially to the thickness of said skin covering and said flange section has an axial dimension essentially corresponding to the thickness of said cortical plate.

6. The combination of an implant for insertion within a hole formed in a bone having a cortical plate and a skin covering of given thicknesses, said implant including:
a screw threaded cross section adapted for receipt within said hole and characterized in that the thread roots and crests thereof are of curvilinear section, wherein the width of said thread roots lies in the range of about 1.5 to 2.5 the width of said thread crests,
a flange section,
a thread block section joining said threaded section and said flange section, said flange section having a transverse dimension exceeding the maximum transverse dimension of said threaded section, as measured across said thread crests, said thread block section having a transverse dimension corresponding essentially to the minimum transverse dimension of said threaded section, as measured across said thread roots, and
a guide section joined to said flange section and extending axially away from said threaded section, said guide section has a transverse dimension less than said flange section, said flange section is formed with a plurality of drive member receiving recesses arranged transversely outwardly of said guide section, said receiving recesses opening axially of said implant and in a direction extending away from said threaded section, and said implant is provided with a mounting opening for said prosthesis attachment, said mounting opening extending through said guide, flange and thread block sections and partially into said threaded section, said mounting opening including a threaded inner portion and a conically shaped outer seal portion; and
said prosthesis attachment including:
a mounting end portion,
a mounting head, and
an intermediate portion for joining said mounting end portion and said mounting head, said mounting end portion having a threaded portion arranged to be threadably coupled with said threaded inner portion and a portion arranged to sealingly engage with said outer seal portion, and said connecting portion is deformable for varying the orientation of said mounting head relative to the axis of said implant.

7. The combination according to claim 6, wherein said guide section has an axial length corresponding essentially to the thickness of said skin covering and said flange section has an axial dimension essentially corresponding to the thickness of said cortical plate, said guide section has a transverse dimension essentially corresponding to said maximum transverse dimension, and said flange section has a conical seal surface converging towards said threaded section.

8. The combination of an implant for insertion within a hole formed in a bone having a cortical plate and a skin covering of given thicknesses, said implant including:
a screw threaded cross section adapted for receipt within said hole and characterized in that the thread roots and crests thereof are of curvilinear section, wherein the width of said thread roots lies in the range of about 1.5 to 2.5 the width of said thread crests,
a flange section,
a thread block section joining said threaded section and said flange section, said flange section having a transverse dimension exceeding the maximum transverse dimension of said threaded section, as measured across said thread crests, said thread block section having a transverse dimension corresponding essentially to the maximum transverse dimension of said threaded section, as measured across said thread roots, and a guide section joined to said flange section and extending axially away from said threaded section, said guide section has a transverse dimension less than said flange section, said flange section is formed with a plurality of drive member receiving recesses arranged transversely outwardly of said guide section, said receiving recesses opening axially of said implant and in a direction extending away from said threaded section, and said implant is provided with a mounting opening for said prosthesis attachment, said mounting opening extending through said guide, flange and thread block sections and partially into said threaded section, at least a portion of said mounting opening is threaded; and said prosthesis attachment includes:

a spacer having a threaded opening extending axially therethrough and a recess disposed concentrically of said threaded opening for slidably receiving said guide section, a spacer connecting screw received within said threaded opening and said portion of said mounting opening for connecting said spacer to said implant, a bushing for attachment to a prosthesis and having a bore opening extending therethrough, and a bushing attachment screw sized to extend through said bore opening and into said threaded opening for clamping said bushing to said spacer.

9. In a method of attaching a prosthesis to a bone, the improvement comprising:

providing a bone implant adapted for attachment to said prosthesis, said implant having a threaded section characterized in that the thread roots and crests thereof are of curvilinear cross section, wherein the width of said thread root lies in the range of about 1.5 to 2.5 the width of said thread crests;

providing a hole in said bone, said hole having a threaded portion characterized as essentially conforming in size and shape to said threaded section, whereby to provide for a friction fit therewith upon threading of said implant into said hole; and threading of said implant into said hole.

10. The implant according to claim 9, wherein said implant additionally includes a flange section having a conically shaped seal surface having a minimum dimension corresponding essentially to a maximum transverse dimension of said threaded section, as measured across said thread crests, and a thread block section joining said flange section to said seal section and having a transverse dimension corresponding essentially to a minimum transverse dimension of said threaded section, as measured across said thread roots; and said hole is formed with a conically shaped outer part providing for surface to surface sealing engagement with said seal surface upon threading of said implant into said hole.

11. The implant according to claim 10, wherein said outer part of said hole is formed with an axial length corresponding essentially to the axial length of said flange section.

* * * * *